(12) United States Patent
Schwarz et al.

(10) Patent No.: US 10,124,187 B2
(45) Date of Patent: Nov. 13, 2018

(54) COMBINATION OF RADIOFREQUENCY AND MAGNETIC TREATMENT METHODS

(71) Applicant: BTL HOLDINGS LIMITED, Nicosia (CY)

(72) Inventors: Tomáš Schwarz, Prague (CZ); Ondra Prouza, Říčany u Prahy (CZ)

(73) Assignee: BTL Holdings Limited, Nicosia (CY)

( * ) Notice: Subject to any disclaimer, the term of this patent is extended or adjusted under 35 U.S.C. 154(b) by 0 days.

(21) Appl. No.: 15/151,012

(22) Filed: May 10, 2016

(65) Prior Publication Data

US 2016/0317827 A1    Nov. 3, 2016

Related U.S. Application Data

(63) Continuation-in-part of application No. 15/073,318, filed on Mar. 17, 2016, now Pat. No. 9,919,161, (Continued)

(51) Int. Cl.
*A61N 2/02* (2006.01)
*A61N 2/00* (2006.01)
(Continued)

(52) U.S. Cl.
CPC .............. *A61N 2/002* (2013.01); *A61N 1/403* (2013.01); *A61B 18/1815* (2013.01);
(Continued)

(58) Field of Classification Search
CPC .................................. A61N 2/02; A61N 2/002
(Continued)

(56) References Cited

U.S. PATENT DOCUMENTS 3,915,151 A * 10/1975 Kraus ................... A61B 17/58
                                                                  600/13
4,237,898 A * 12/1980 Whalley ................. A61N 1/40
                                                                  607/99
(Continued)

FOREIGN PATENT DOCUMENTS

EP        0209246 A1    1/1987
EP        2676700 A2   12/2013
(Continued)

OTHER PUBLICATIONS

Lin, et al., "Functional Magnetic Stimulation: A New Modality for Enhancing Systemic Fibrinolysis," Arch Phys Med Rehabil vol. 80, May 1999, pp. 545-550.
(Continued)

*Primary Examiner* — Samuel Gilbert
(74) *Attorney, Agent, or Firm* — Kenneth H. Ohriner; Perkins Coie LLP

(57) ABSTRACT

Devices and methods for contactless skin treatment use feedback power control for non-invasive treatment of skin and human tissue. Electromagnetic energy heats skin or tissue. A feedback system measures an output physical quantity before the output of electromagnetic waves from the device into the patient. Alternatively the feedback system scans values of a physical quantity on or near the patient. The devices and methods allow for delivering the optimum amount of energy to the patient while reducing the thermal load of the device. Methods and an apparatus for treatment of target biological structure by combination of magnet treatment and electromagnetic treatment. The method and apparatus may be used for aesthetic applications, e.g. cellulite treatment, body shaping, skin rejuvenation or enhancing skin appearance.

30 Claims, 9 Drawing Sheets

Related U.S. Application Data which is a continuation-in-part of application No. 14/951,093, filed on Nov. 24, 2015, now abandoned, which is a continuation-in-part of application No. 14/926,365, filed on Oct. 29, 2015, now abandoned, which is a continuation-in-part of application No. 14/789,658, filed on Jul. 1, 2015, now Pat. No. 9,636,519, which is a continuation-in-part of application No. 14/873,110, filed on Oct. 1, 2015, now Pat. No. 9,586,057, which is a continuation of application No. 14/789,156, filed on Jul. 1, 2015, application No. 15/151,012, which is a continuation-in-part of application No. 15/099,274, filed on Apr. 14, 2016, now abandoned, which is a continuation-in-part of application No. 14/697,934, filed on Apr. 28, 2015, now Pat. No. 9,468,774, which is a continuation-in-part of application No. 14/700,349, filed on Apr. 30, 2015, now Pat. No. 9,446,258.

(51) Int. Cl.
*A61N 1/40* (2006.01)
*A61N 5/02* (2006.01)
*A61B 18/18* (2006.01)
*A61B 18/00* (2006.01)
*A61B 18/14* (2006.01)
*A61B 18/20* (2006.01)
*A61N 2/06* (2006.01)

(52) U.S. Cl.
CPC ..... *A61B 18/20* (2013.01); *A61B 2018/00464* (2013.01); *A61B 2018/00476* (2013.01); *A61B 2018/147* (2013.01); *A61N 2/006* (2013.01); *A61N 2/02* (2013.01); *A61N 2/06* (2013.01); *A61N 5/025* (2013.01)

(58) Field of Classification Search
USPC ....................................... 600/9–15
See application file for complete search history.

(56) References Cited

U.S. PATENT DOCUMENTS

| | | | |
|---|---|---|---|
| 4,315,503 A | 2/1982 | Ryaby et al. | |
| 4,665,898 A | 5/1987 | Costa | |
| 4,993,413 A | 2/1991 | McLeod | |
| 5,085,626 A | 2/1992 | Frey | |
| 5,401,233 A | 3/1995 | Erickson et al. | |
| 5,766,124 A | 6/1998 | Polson | |
| 5,807,232 A | 9/1998 | Espinoza et al. | |
| 5,984,854 A | 11/1999 | Ishikawa et al. | |
| 6,063,108 A | 5/2000 | Salansky et al. | |
| 6,117,066 A | 9/2000 | Abrams | |
| 6,179,769 B1 | 1/2001 | Ishikawa et al. | |
| 6,213,933 B1 | 4/2001 | Lin | |
| 6,223,750 B1 | 5/2001 | Ishikawa et al. | |
| 6,402,678 B1 | 6/2002 | Fischell et al. | |
| 6,418,345 B1 | 7/2002 | Tepper et al. | |
| 6,527,694 B1 | 3/2003 | Ishikawa et al. | |
| 6,569,078 B2 | 5/2003 | Ishikawa et al. | |
| 6,939,287 B1 | 9/2005 | Ardizzone et al. | |
| 7,030,764 B2 | 4/2006 | Smith et al. | |
| 7,601,115 B2 | 10/2009 | Riehl | |
| 7,740,574 B2 | 6/2010 | Pilla et al. | |
| 7,744,523 B2 | 6/2010 | Epstein | |
| 7,946,973 B2 | 5/2011 | Peterchev | |
| 7,998,053 B2 | 8/2011 | Aho | |
| 8,088,058 B2 | 1/2012 | Juliana et al. | |
| 8,979,727 B2* | 3/2015 | Ron Edoute | A61N 1/328 600/14 |
| 9,002,477 B2 | 4/2015 | Burnett | |
| 2001/0031906 A1* | 10/2001 | Ishikawa | A61N 2/008 600/13 |
| 2003/0158585 A1 | 8/2003 | Burnett | |
| 2006/0152301 A1* | 7/2006 | Rohwedder | B06B 1/0215 333/105 |
| 2006/0187607 A1 | 8/2006 | Mo | |
| 2008/0249350 A1 | 10/2008 | Marchitto et al. | |
| 2008/0262287 A1 | 10/2008 | Dussau | |
| 2009/0005631 A1* | 1/2009 | Simenhaus | A61N 2/002 600/9 |
| 2010/0036368 A1 | 2/2010 | England et al. | |
| 2010/0087699 A1 | 4/2010 | Peterchev | |
| 2010/0121131 A1 | 5/2010 | Mathes | |
| 2010/0179372 A1* | 7/2010 | Glassman | A61N 5/0616 600/9 |
| 2010/0331603 A1 | 12/2010 | Szecsi | |
| 2011/0021863 A1 | 1/2011 | Burnett | |
| 2011/0077451 A1 | 3/2011 | Marchitto et al. | |
| 2011/0263925 A1* | 10/2011 | Bratton | A61N 2/004 600/14 |
| 2012/0053449 A1 | 3/2012 | Moses | |
| 2013/0030239 A1* | 1/2013 | Weyh | A61N 2/006 600/14 |
| 2013/0123568 A1 | 5/2013 | Hamilton et al. | |
| 2013/0137918 A1 | 5/2013 | Phillips et al. | |
| 2013/0150653 A1 | 6/2013 | Borsody | |
| 2013/0158634 A1 | 6/2013 | Edoute | |
| 2013/0238061 A1 | 9/2013 | Edoute | |
| 2013/0317281 A1 | 11/2013 | Schneider | |
| 2014/0046423 A1 | 2/2014 | Rajguru | |
| 2014/0330067 A1 | 11/2014 | Jordan | |
| 2015/0025299 A1 | 1/2015 | Edoute | |
| 2015/0123661 A1 | 5/2015 | Yui | |
| 2015/0133717 A1 | 5/2015 | Ghiron | |
| 2015/0157873 A1 | 6/2015 | Sokolowski | |
| 2015/0216719 A1* | 8/2015 | DeBenedictis | A61F 7/007 601/2 |
| 2015/0328475 A1 | 11/2015 | Kim et al. | |
| 2015/0367141 A1 | 12/2015 | Goetz | |
| 2016/0030763 A1 | 2/2016 | Midorikawa et al. | |
| 2016/0051827 A1 | 2/2016 | Edoute | |
| 2016/0250494 A1 | 9/2016 | Sakaki et al. | |

FOREIGN PATENT DOCUMENTS

| | | |
|---|---|---|
| WO | 2002025675 A1 | 3/2002 |
| WO | 2003090863 A1 | 11/2003 |
| WO | 2004087255 A1 | 10/2004 |
| WO | 2008109058 A1 | 9/2008 |
| WO | 2010007614 A3 | 1/2010 |
| WO | 2010135425 A1 | 11/2010 |
| WO | 2015012672 A1 | 1/2015 |

OTHER PUBLICATIONS

European Patent Office, International Search Report and Written Opinion for International Application No. PCT/IB2016/053930; dated Dec. 12, 2016; 19 pages.

Polk, "Therapeutic Applications of Low-Frequency Sinusoidal and Pulsed Electric and Magnetic Fields," The Biomedical Engineering Handbook, vol. 1, 2000, Second edition, pp. 1625-1636.

\* cited by examiner

US 10,124,187 B2

COMBINATION OF RADIOFREQUENCY AND MAGNETIC TREATMENT METHODS

PRIORITY CLAIM

This application is a Continuation-in-Part of each of the following: U.S. patent application Ser. No. 15/073,318 filed Mar. 17, 2016 and; Ser. No. 14/951,093 filed Nov. 24, 2015 and now pending; Ser. No. 14/926,365 filed Oct. 29, 2015 and now pending; and Ser. No. 14/789,658 filed Jul. 1, 2015 and now pending. This application is also a Continuation-in-Part of U.S. patent application Ser. No. 14/873,110 filed Oct. 1, 2015 and now pending, which is a Continuation of U.S. patent application Ser. No. 14/789,156 filed Jul. 1, 2015 and now abandoned. This application is also a Continuation-in-Part of U.S. patent application Ser. No. 15/099,274 filed Apr. 14, 2016 and now pending.

This application is also a Continuation-in-Part of U.S. patent application Ser. No. 14/697,934 filed Apr. 28, 2015 and now pending; and of Ser. No. 14/700,349 filed Apr. 30, 2015 and now pending.

Each of these applications is incorporated herein by reference.

FIELD OF THE INVENTION

The present invention generally relates to aesthetic methods for enhancing the visual appearance of a patient by stimulation using time-varying and high-power magnetic field based on a high value of magnetic flux density and/or high repetition rate.

BACKGROUND OF THE INVENTION

Aesthetic medicine includes all treatments resulting in enhancing a visual appearance and satisfaction of the patient. Patients want to minimize all imperfections including body shape and effects of natural aging. Indeed, patients request quick, non-invasive procedures providing satisfactory results with minimal risks.

The most common methods used for non-invasive aesthetic applications are based on application of mechanical waves, e.g. ultrasound or shock wave therapy; or electromagnetic waves, e.g. radiofrequency treatment or light treatment, such as intense pulsed light or laser treatment. The effect of mechanical waves on tissue is based especially on cavitation, vibration and/or heat inducing effects. The effect of applications using electromagnetic waves is based especially on heat production in the biological structure.

Skin tissue is composed of three basic elements: epidermis, dermis and hypodermis or so called subcutis. The outer and also the thinnest layer of skin is the epidermis. The dermis consists of collagen, elastic tissue and reticular fibres. The hypodermis is the lowest layer of the skin and contains hair follicle roots, lymphatic vessels, collagen tissue, nerves and also fat forming a subcutaneous white adipose tissue (SWAT). The fat cells create lobules which are bounded by connective tissue, fibrous septa (retinaculum cutis).

Another part of adipose tissue, so called visceral fat, is located in the peritoneal cavity and forms visceral white adipose tissue (VWAT) located between parietal peritoneum and visceral peritoneum, closely below muscle fibres adjoining the hypodermis layer.

SUMMARY OF THE INVENTION

A method of treating a biological structure uses a combination of non-invasive methods for enhancing human appearance. The invention utilizes electromagnetic radiation. Methods may be used for targeted remodeling adipose tissue, focused treatment of cellulite, body contouring, skin tightening or skin rejuvenation. The invention relates to focused heating of the target tissue by electromagnetic waves, whereas the effect of focused heating of the target tissue is amplified by the effect of a pulsed magnetic field treatment.

Glossary

Biological structure is at least one neuron, neuromuscular plate, muscle fiber, adipocyte, collagen, elastin, pigment or skin.

Remodeling target biological structure refers to reducing the number and/or volume of the adipocytes by apoptosis and/or necrosis, cellulite treatment, body shaping and/or contouring, muscle toning, skin tightening, collagen treatment, skin rejuvenation, wrinkle removing, reducing stretchmarks, breast lifting, lip enhancement, treatment of vascular or pigmented lesions of the skin or hair removing.

Adipose tissue refers to at least one lipid rich cell, e.g. adipocyte.

Bolus refers to a layer of fluid material, e.g. water or fluid solution of ceramic particles, preferably enclosed in a flexible sac made of biocompatible material.

Impulse refers to a single magnetic stimulus.

Pulse refers to a period of stimulation by a magnetic field of at least one magnetic stimulus and time duration of no stimulation, i.e. time duration between two impulses from rise/fall edge to next rise/fall edge.

As used here "continual therapy" and "continual magnetic stimulation" means therapy where the set of the magnetic flux density and frequency/repetition rate of magnetic pulses does not lead to exceeding of the operating temperature 43° C. on the casing of the device operating in an ambient temperature of 30° C. regardless of the duration of therapy.

DETAILED DESCRIPTION

Figure 1:
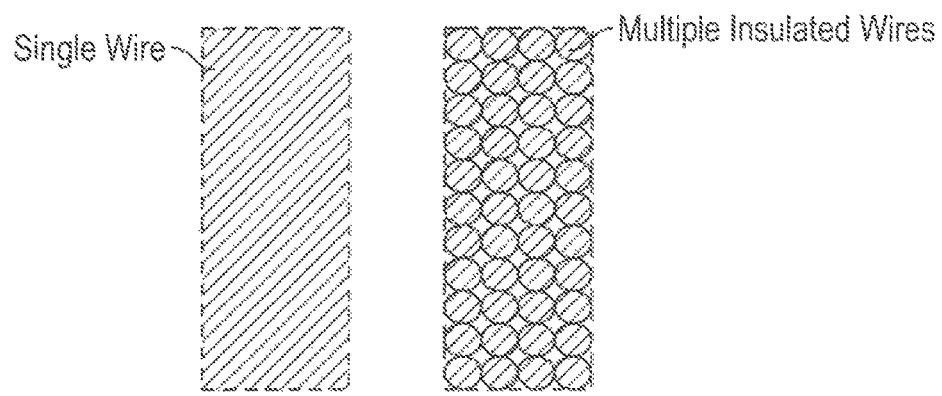
FIG. 1 is a cross section view of a coil winding.

During last few decades patient have not only wanted to be in good health, they have also wanted to look-well, i.e. to be well-shaped, without any unattractive fat and to have a young appearance, without wrinkles, stretchmarks or sagging breasts. This has resulted in a progressive evolution of invasive aesthetic methods such as aesthetic surgery removing and remodeling the human body by invasive and potentially dangerous methods, e.g. liposuction or implants. The side effect of invasive methods may be scars. The side effects resulted in the rapid progress in non-invasive method, e.g. lipolysis or removing skin imperfections.

The present method may be used for remodeling the adipose tissue, body shaping and/or contouring, muscle toning, skin tightening, skin rejuvenation, wrinkle removing, reducing stretchmarks, breast lifting, lip enhancement or treatment of cellulite in general by application of electromagnetic radiation to target structure to selectively heat the target tissue to remove and/or remodel adipose tissue from the target tissue. The second approach is to transmit a magnetic stimulation to the target structure, inducing at least partial muscle contraction within the target structure to remodel the adipose tissue by natural adipose tissue catabolism. Adipose tissue catabolism may be caused by apoptosis or necrosis of the adipocytes. The muscle contraction caused by induced eddy current is the same as a natural contraction. The adipose tissue may be reduced in natural way. Additionally, the muscle may be shredded in a natural way. Therefore the effect results in body shaping and/or contouring may be significantly improved.

The method causes the circumferential reduction i.e. a reduction of the size of the treated body area. The method is mostly indicated for the regions with cellulite, especially for buttocks, abdomen, hips, thighs or arms. However, the indication is not limited to the mentioned regions and the method may be used for stimulation of any other body area.

The present invention discloses the advanced approaches in aesthetic applications, e.g. for cellulite treatment and/or body shaping. Combined methods of treatment by electromagnetic field and treatment by magnetic field are used. The electromagnetic field may include treatment by radiofrequency, infrared or optical waves. The magnet treatment may be provided by permanent magnets, electromagnetic devices generating a static magnetic field or time-varying magnetic devices. In the preferred application the treatment by a pulsed magnetic field and radiofrequency treatment may be combined. However the application is not limited by the recited combination so the combined method may include magnet treatment and any treatment by electromagnetic field, e.g. light treatment, IR treatment or treatment by radiofrequency waves, e.g. microwaves, short waves or long waves.

The present invention discloses a method and a technical solution of application of different approaches of aesthetic treatments, e.g. magnet treatment and radiofrequency treatment. U.S. patent application Ser. No. 14/278,756 incorporated herein by reference describes a device which may be used. In an alternative embodiment the radiofrequency treatment device may exclude the balun transformer, or the balun transformer may be included in transmatch. The possible methods of treatment by combined methods are described below.

FIG. 1 illustrates a cross section of winding of a coil for a magnetic stimulation device. The coil may be constructed from litz-wire, wherein each wire is insulated separately. Each individual conductor is coated with non-conductive material so the coil constitutes multiple insulated wires. Unlike existing magnetic coil conductors, the present coil is not made of bare wire e.g. litz-wire without insulation, or conductive tapes, conductive strips, or copper pipe with hollow inductors. The insulation of wires separately is a substantial improvement, since this leads to a significant reduction of the induced eddy currents. Power loss due to eddy currents, per single wire, is described by Equation 1 below. The small diameter wires of the present coil significantly reduce self-heating of the coil and therefore increases efficiency of the present magnetic stimulation device:

$$P_{EDDY} = \frac{\pi^2 \cdot B_p^2 \cdot d^2 \cdot f^2}{6 \cdot k \cdot \rho \cdot D}, \quad \text{Eq. 1}$$

where: $P_{EDDY}$ is power loss per unit mass (W·kg$^{-1}$); $B_p$ is the peak of magnetic field (T); f is frequency (Hz); d is the thickness of the sheet or diameter of the wire (m); k is constant equal to 1 for a thin sheet and 2 for a thin wire; $\rho$ is the resistivity of material ($\Omega$·m); D is the density of material (kg·m$^3$).

The individual insulation of each wire reduces eddy currents. The individually insulated wires may be wound either one by one or in a bundle of individually insulated wires so as to form a coil, which will serve as a magnetic field generator. The coil provides an improvement in the efficiency of energy transfer in the LC resonant circuit and also reduces or eliminates unwanted thermal effects.

The coil may have a planar coil shape where the individually insulated wires may have cross-section wires with conductor diameter less than 3 mm even more preferably less than 0.5 mm and most preferably less than 0.05 mm. The wires are preferably made of materials with higher density and higher resistivity e.g. gold, platinum or copper. The diameters of the single wires should be minimal. On the other hand the total diameter should be maximal because of inverse proportion between the cross-section of all wires forming the coil and the electrical resistance. Therefore the ohmic part of the heat is then lower. Eq. 2 describes power loss of the coil:

$$P_R = \frac{\rho \cdot \frac{l}{S} \cdot I^2}{m} \quad \text{Eq. 2}$$

Where: $P_R$ is the power loss heat dissipation (W); $\rho$ is the resistance ($\Omega$·m); l is the length of wire (m); S is the surface area (m$^2$); l is the current (A) and m is 1 kg of wire material.

Total power loss is (Eq.3):

$$P_{TOT} = P_{EDDY} + P_R, \quad \text{Eq. 3}$$

Where: $P_{TOT}$ is the total power losses (W·kg$^{-1}$); $P_{EDDY}$ is the power dissipation of eddy currents (W·kg$^{-1}$); $P_R$ is the power loss heat dissipation (W·kg$^{-1}$).

Dynamic forces produced by current pulses passing through the wires of the coil cause vibrations and unwanted noise. The individual insulated wires of the coil may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the coil provided as a solid mass, the vibrations and resonance caused by movements of the individual insulated wires are suppressed. Therefore noise is reduced.

The coil may be attached to the case of the applicator, such as a hand held applicator of the magnetic stimulation device; built-in applicator in e.g. chair, bed; or stand-alone applicator e.g. on mechanical fixture. The attachment may be provided by an elastic material e.g., silicone, gum; or other flexible manner. Connection with the coil of the applicator's case can be ensured by several points. The several fastening points ensure the connection of the coil to the casing by flexible material so that the main part of the coil and the main part of the casing of applicator are spaced apart. The spacing should be at least 0.1 mm so that air can easily flow. The gap between the coil and the casing can be used either for spontaneous or controlled cooling. The coil may optionally be connected to the case of the applicator by only one fastening point. The fastening points eliminate vibrations of wires which could be transferred to housing of the applicator and therefore reduce noise of the magnetic stimulation device.

Figure 2:
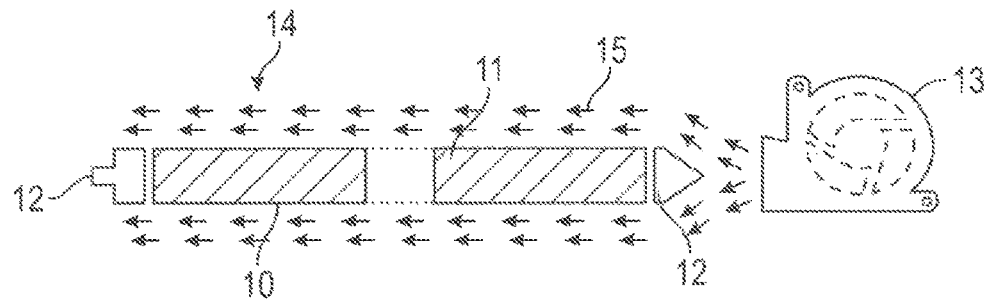
FIG. 2 is an illustrative embodiment of cross-section of the magnetic applicator.

FIG. 2 is a cross-section of the magnetic applicator which allows better flow on the lower and upper sides of the coil and thus more efficient heat dissipation. The magnetic stimulation device includes a coil 10, the circuit wires 11 and the fastening points 12 for connection of the coil to the casing of the applicator (not shown). The fastening points 12 are preferably made of flexible material however the rigid material may be used as well. The fastening points 12 may be located on the outer circumferential side of the coil. However, alternatively it is possible to put these fastening points to a lower or upper side of the coil.

The fastening points 12 connect the coil to the case of the applicator in at least one point. The fastening points 12 maintain the coil and the main part of the case of the applicator spaced apart so that fluid (which may be air or any liquid) can flow between them. At least one blower 13 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown) can ensure connection of the applicator 14 with the energy source and/or control unit of magnetic stimulation device. The connecting tube may also contain a conduit of the fluid.

The arrows 15 indicate the air flow through the applicator 14. This arrangement of the blower allows the air to bypass the coil from upper and lower (patient's) side. Outlet may be preferably placed on upper side of the casing. By placing the blower around the circumference of the coil instead of on the top/below the coil, the blower 13 does not interfere with the magnetic flux peak and therefore its lifespan and reliability is increased.

Figure 3:
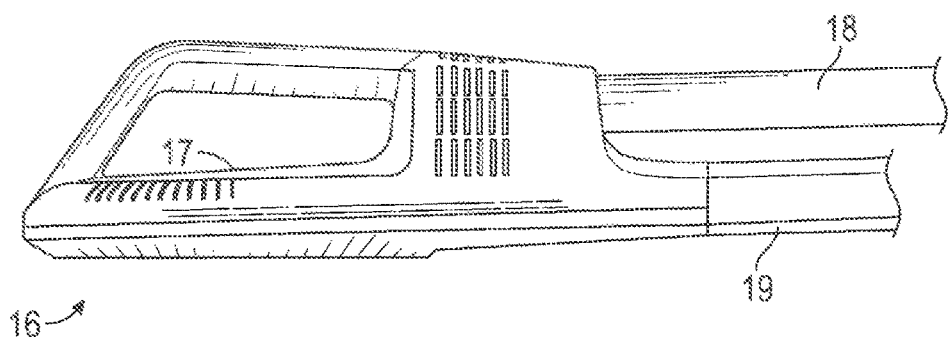
FIG. 3 is an illustrative embodiment of a casing of the magnetic applicator.

FIG. 3 is an illustrative embodiment of a casing of the magnetic applicator. The overview drawing contains casing itself 16, which might contain an outlet 17 preferably placed on upper side of the casing 16. A connecting tube 18 may not only ensure connection of the applicator with the energy source and/or control unit of magnetic stimulation device, but also connection to a source of the fluid; however the conduit of the fluid 19 may also be connected separately.

Figure 4A:
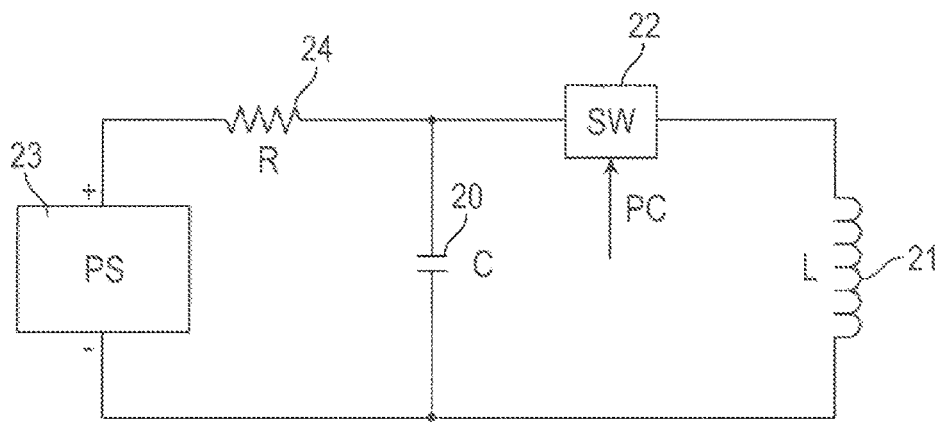
FIGS. 4A and 4B illustrates circuits for providing high power pulses to a stimulating coil.
Figure 4B:
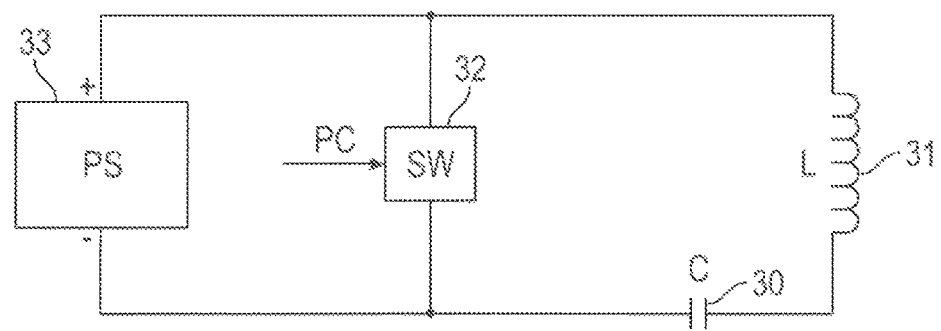

FIG. 4A and FIG. 4B illustrate circuits for providing high power pulses to the stimulating coil. FIG. 4A shows a circuit for providing high power magnetic pulses. FIG. 4B shows a circuit for providing high power pulses.

Existing magnetic stimulation devices achieve magnetic flux density of a few tenths to several Teslas. To achieve this level of magnetic flux density, the energy source used generates sufficient voltage. This voltage can reach thousands of volts. In FIG. 4A the circuits for providing high power pulses to the stimulating coil contain a series connection to the switch 22 and the coil 21. The switch 22 and the coil 21 together are connected in parallel with an energy storage device 20. The energy storage device 20 is charged by the energy source 23 and the energy storage device 20 then discharges through the switching device 22 to the coil 21.

During second half-period of LC resonance, the polarity on the energy storage device 20 is reversed in comparison with the energy source 23. In this second half-period, there is a conflict between energy source 23, where voltage on positive and negative terminals is typically thousands of Volts. The energy storage device 20 is also charged to the positive and negative voltage generally to thousands of Volts. As a result, there is in the circuit, consequently, twice the voltage of the energy source 23. Hence the energy source 23 and all parts connected in the circuit are designed for a high voltage load. Therefore, the protective resistors and/or protection circuitry 24 must be placed between energy source 23 and energy storage device 20. As a result a large amount of energy is transformed to undesired heat in the protective resistors and/or protection circuitry 24.

FIG. 4B shows a circuit for providing high power pulses for improved function of the magnet stimulation device. The coil 31 and an energy storage device 30 are connected in series and disposed in parallel to the switch 32. The energy storage device 30 is charged through the coil 31. To provide an energy pulse, controlled shorting of energy source 33 takes place through the switch 32. In this way the high voltage load at the terminals of the energy source 33 during the second half-period of LC resonance associated with known devices is avoided. The voltage on the terminals of energy source 33 during second half-period of LC resonance is a voltage equal to the voltage drop on the switch 32.

The switch 32 can be any kind of switch such as diode, MOSFET, JFET, IGBT, BJT, thyristor or their combination. Depending on the type of component the load of energy source 33 is reduced to a few Volts, e.g., 1-10 volts. Consequently, it is not necessary to protect the energy source 33 from a high voltage load, e.g., thousands of Volts. The use of protective resistors and/or protection circuits is reduced or eliminated. The present designs simplify the circuits used, increase efficiency of energy usage and provide higher safety.

Figure 5:
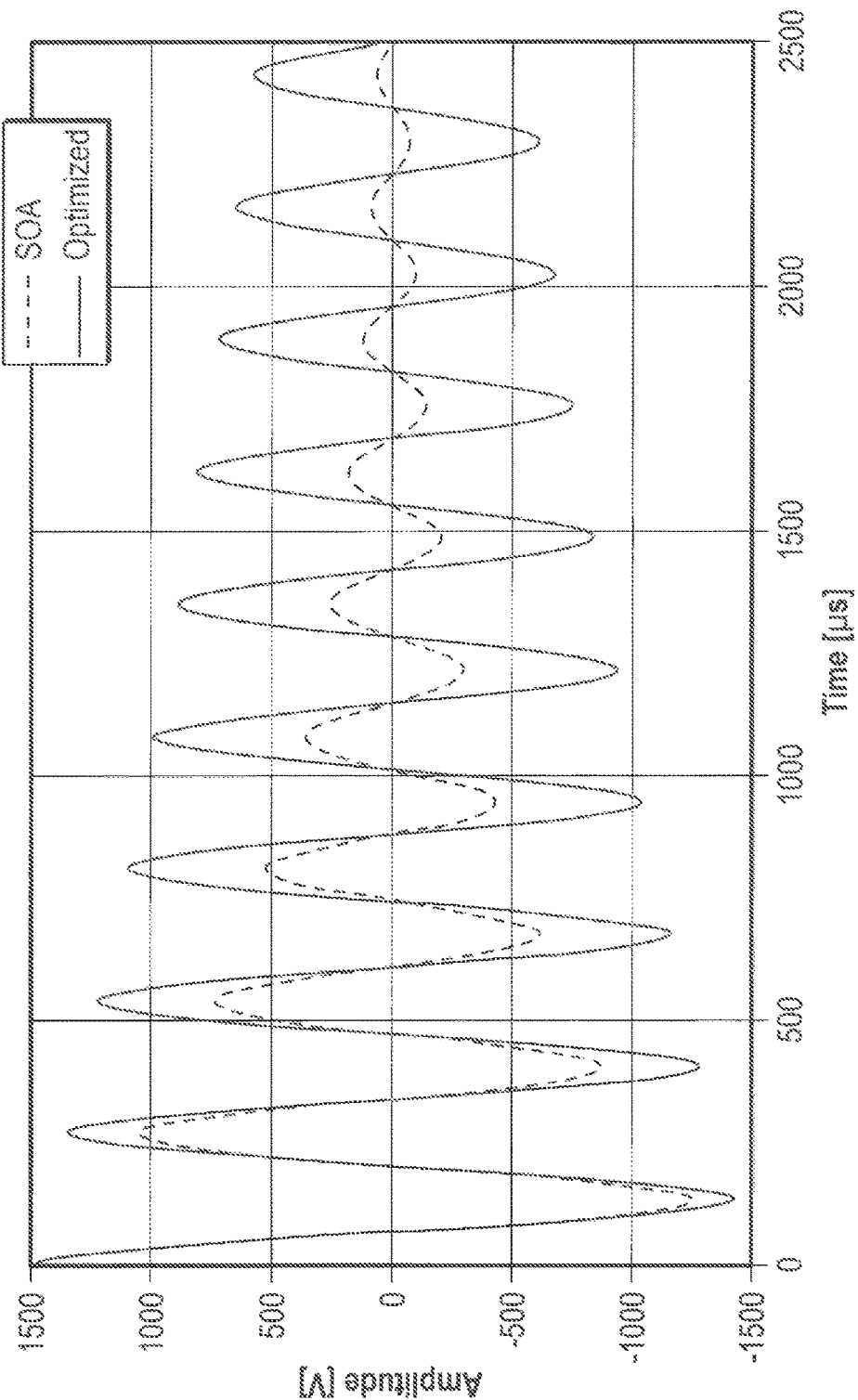
FIG. 5 is a graph showing voltage drop in the energy storage device.

FIG. 5 show an exponential voltage drop in the energy storage device. Energy savings during time-varying magnetic therapy may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the device up to hundreds of magnetic pulses per second without the need to increase the input power. The voltage drop between any of the successive amplitudes is not higher than 21%, even more preferably not higher than 14% and most preferably not higher than 7%.

The device can be used for treatment/successive treatments in continual, interrupted or various duty cycle regime. The duty cycle may be higher than 10%, which means interrupted regime with the ratio up to 1 active to 9 passive time units. The ratio may possibly change during the therapy. The device enables operation defined by the peak to peak magnetic flux density on the coil surface at least 3 T, more preferably at least 2.25 T, most preferably at least 1.5 T at repetition rates above 50 Hz, more preferably at repetition rates above 60 Hz, even more preferably at repetition rates above 70, most preferably at repetition rates above 80 Hz with treatment/successive treatments lasting several seconds or longer, for example, for at least 5, 10, 30, 60, 120 or 240 seconds, or longer. The total power consumption is below 1.3 kW and the width of pulses is in the range of hundreds of µs.

The device enables achieving repetition rates above 100 Hz, more preferably repetition rates above 150 Hz, most preferably repetition rates above 200 Hz with the magnetic flux density providing a therapeutic effect on neurons and/or muscle fibers and/or endocrine cells (e.g. at least partial muscle contraction, action potential in cell). Based on achievement of repetition rates in order of few hundreds the device also enables assembling the magnetic pulses into the various shapes (e.g. triangular, rectangular, exponential), with the shape widths from 6 ms to several seconds or longer.

Figure 6:
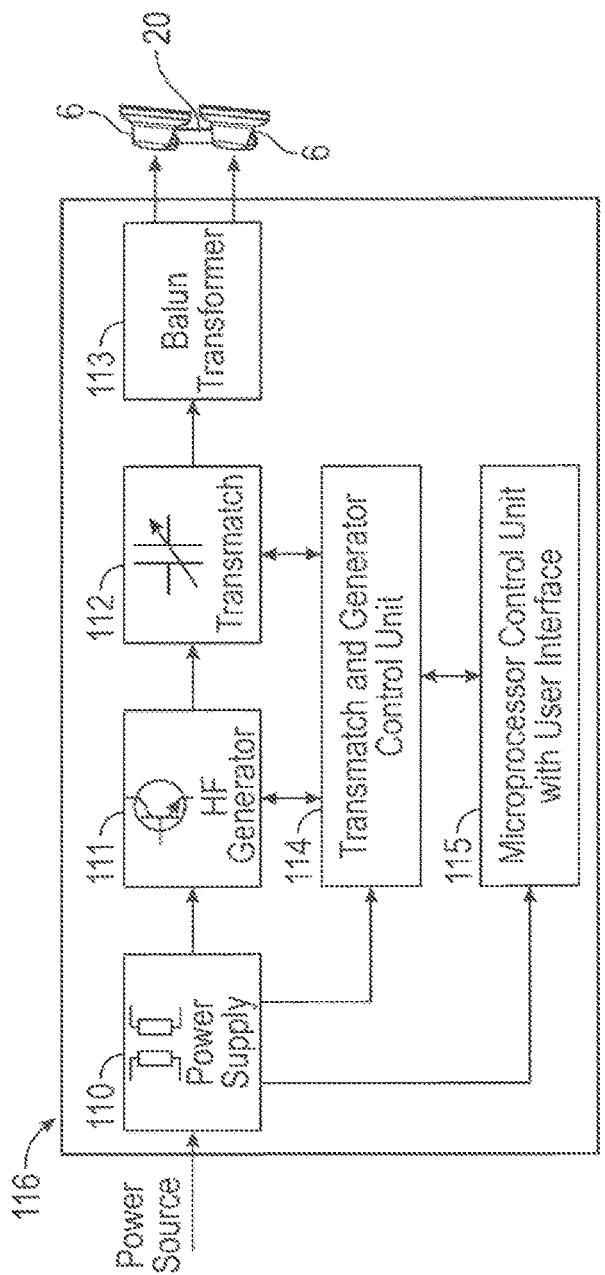
FIG. 6 is a schematic diagram of a system for controlled deep heating of sub dermal tissues.

Referring now to FIG. 6, a system 116 applies electromagnetic energy through a skin layer, such as the epidermis, and to the underlying dermal and/or sub dermal tissue, and underlying collagen tissue, causing acceleration of lipolysis and collagen remodeling. The system may include 6 blocks. The power supply 110 is connected to a power source. An HF generator (high frequency generator) 111 and a transmatch and generator control unit 114, and a microprocessor control unit with user interface 115, are connected to the power supply 110. The HF generator 111 may generate an electromagnetic field at 13.56 or 40.68 or 27.12 MHz, or 2.45 GHz or optionally at other frequencies as well. The 13.56, 27.12 and 40.68 MHz and 2.45 GHz frequencies avoid creating radio interference, as these frequencies are exclusively assigned as free or open frequencies.

The microprocessor control unit with user interface 115 provides communication between the transmatch and generator control unit 114 and user interface, which may be a touch screen on the device display.

The transmatch and generator control unit 114 receives information from the operator via the control unit and regulates the operation of the HF generator 111 and the transmatch 112. The transmatch transmits HF to a balun transformer 113, which converts unbalanced impedance to balanced impedance. This processed signal goes to two capacitive applicators 6, which may be positioned 0.5 cm or higher above the surface of the skin or applied on dielectric or insulating, non-conductive material which is in contact with the skin surface.

Figure 7:
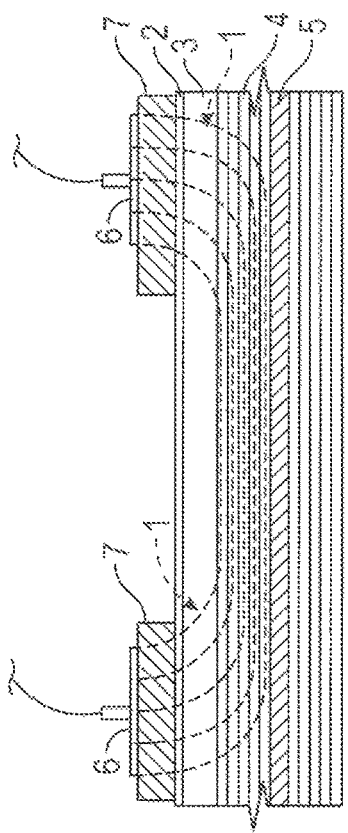
FIG. 7 is a schematic view of a trans-regional course of electromagnetic field.

FIG. 7 is a schematic representation of a heat distribution under the skin. One or more applicators 6 create an electromagnetic field. This electromagnetic field crosses through the skin 2, subcutaneous fat 3 and muscle 4 or the bone 5. Capacitive applicators 6 provide deep heating, which heats selectively only structures with low volume, of water. A spacer 7 such as a towel, gauze pad, foam pad, cloth pad and another porous or air permeable materials may be placed on the skin, with the applicator then placed on top of the spacer 7. The spacer may be made from three-dimensional material with high air permeability formed by two square fabrics with preferably low square densities connected by tough filaments. This automatically sets the separation distance between the applicator and the skin, and prevents the applicator from touching the skin. The spacer 7 may be made of various dielectric or electrically non-conductive materials. The spacer 7 is typically dry in use. Alternatively, a reusable or a disposable spacer may be attached to the applicator. For example, the spacer may comprise posts, a frame, or other structure on the applicator that contacts the skin, while keeping the active surface of the applicator spaced apart from the skin. As described and claimed here, such spacing elements are additional elements and not part of applicator. The methods may be performed with no part or surface of the actuator in contact with the skin.

A selective heating process is observed in the dermis 3 due to dielectric losses of induced electromagnetic field. Dielectric loss is created, as part of an AC electromagnetic field power is converted to heat in the dielectric. During this process, ions accelerate and collide, polar molecules rotate, non-polar molecules undergo distortion and these movements produce thermal energy. Skin and muscle, are largely not affected by electromagnetic field 1 as they contain water and the blood, circulation provides for cooling. Bone 5 gets little if any heating because the applicators 6 are positioned to create a field only on the upper structures. The lipid cells of the adipose tissue contain less water than the surrounding tissue and are therefore heated at higher level than the surrounding tissue.

Electrodes can be placed coplanar, tilted to each other or parallel to each other. Coplanar electrodes can be advantageously (but not exclusively) used for heating the shallow layers of human skin. In this arrangement the electromagnetic waves tend to travel through materials with the lowest impedance, such as epidermis and dermis. This effect may be favorably used for remodeling subcutaneous collagen and elastin fibers.

Electrodes tilted to each other can be advantageously used for different sized patients, limbs or another body parts. Electrodes parallel to each other can be advantageously (but not exclusively) used for heating adipose tissue. In this arrangement adipose fat tissue acts as sub cutis layer with highest impedance and therefore transforms most of induced electromagnetic energy to heat.

In coplanar or tilted arrangement of electrodes, more distance between electrodes induces more energy in deep tissues of patient's skin, which is desirable for subcutaneous adipose tissue heating. The electrodes may be used one by one in one plane distanced at least 6 cm. This can be obtained by distribution of electrodes in predetermined minimal distance or by a matrix or array of electrodes that are switched so that adjoining electrodes are not powered on at the same time. Therefore, a specified minimal distance between electrodes will be maintained. Shorter distances between electrodes may be advantageous for treatment of shallow layers of patient's skin.

Figure 8:
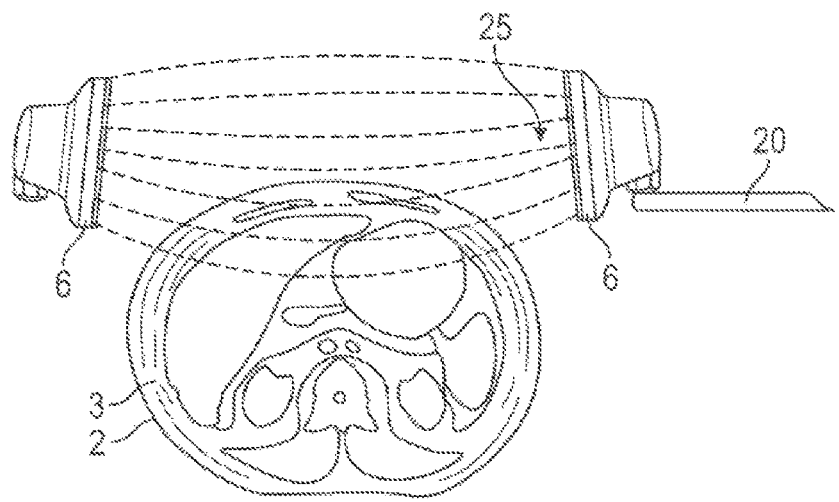
FIGS. 8 and 9 are schematic examples of positioning of electrodes shown in FIG. 1.
Figure 9:
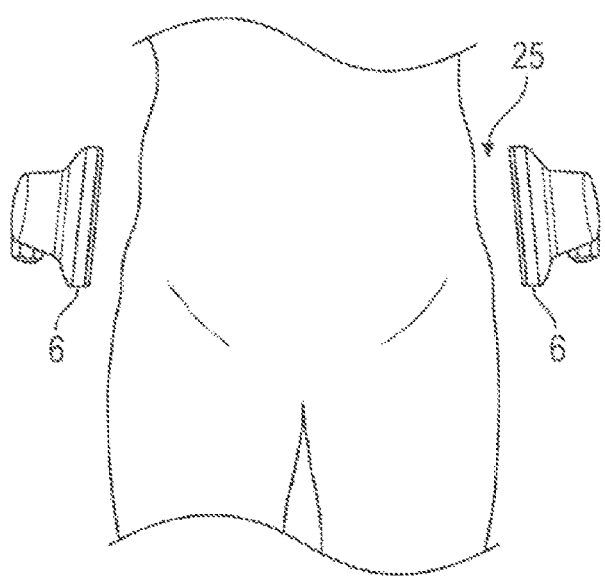

FIGS. 8 and 9 are schematic examples of positioning of the applicators or electrodes 6 providing radiant energy through the skin 2 to subcutaneous fat 3. The applicator includes one or more electrodes and wiring connections to system components. The electrodes are positioned approximately 2-3 cm above the surface of the skin and separated from the skin by an air gap 25, or placed onto a spacer 7 which is in contact with the skin surface, as shown in FIG. 7. The spacer 7, if used, may correspondingly typically be about 0.5 to 1 cm thick. The applicator 6 may be temporarily fixed in position relative to the patient, if desired, for example on a mechanical fixture or holder. It is not necessary in each instance for the applicator to be continuously moving during the procedure. This makes the procedure easier to perform, since user need not constantly keep moving the applicator over the patient's skin. Consequently, the user can accordingly simultaneously attend to other needs of a patient. The applicator 6 may have a relatively large surface area, so that the field 1 is distributed more widely through the subcutaneous tissue. For example, the applicator may have a surface area of at least about 15, 30, 50, 100, or 150 square centimeters.

If more than one applicator is used, applicators may be positioned on opposite sides of the patient. A spacer may be positioned between one or more applicator and the skin of the patient. The electromagnetic waves may be transmitted in the range of 13.553-13.567 or 26.957-27.283 or 40.66-40.70 MHz or 2.4-2.5 GHz from the applicator into the subcutaneous tissue. The temperature of the skin surface may be increased to about 32-45° C.

One or more of the applicators may have a temperature sensor which measures and monitors the temperature of the treated tissue. Temperature can be analyzed by a microprocessor control unit. The temperature sensor may be a contactless sensor (e.g. infrared temperature sensor), contact sensor (e.g. resistance temperature detector) or invasive sensor (e.g. a thermocouple) for exact temperature measuring of deep or shallow tissue of human skin. The microprocessor controller may use algorithms to calculate the deep or shallow temperature based on the surface temperature of the skin. A feedback system may be used to measure and control temperatures on the skin surface or below the skin surface. The feedback system may control the temperature to a predetermined level, for example by adjusting power, airflow circulation, phase shifting, supplemental magnetic field, and perhaps other parameters, or combinations of them.

Figure 10:
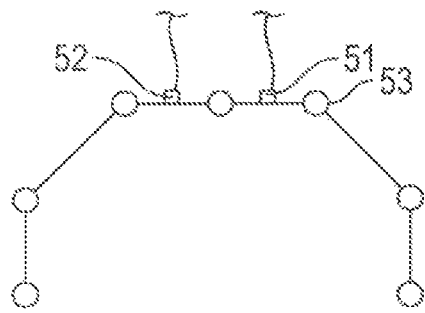
FIG. 10 is schematic diagram of an alternative electrode design.

FIG. 10 illustrates arrangement of a mechanical fixture or holder for tilting electrodes which enables treatment of different sized patients, limbs or other body parts. A tilting device may include at least two electrodes 51, 52 connected by joints 53, allowing the electrodes to be spatially adjustable. Each electrode may further enable connection of additional electrodes, so that the applicator can be extended according to the needs of the particular patient. The joint connection with additional electrode(s) may be a plug and play device. The microprocessor control unit may be programmed to recognize the additional electrodes and allow the user to select a therapy with regard to the number of participating electrodes. In some embodiments the radiofrequency device also enables shifting of electrodes for example by parallelogram or simply by fastening of each electrode on mechanical fixture or holder. In another embodiment the arrangement of mechanical fixture or holder enables tilting and shifting of electrodes.

Substantially coplanar electrodes may be advantageous for treatment of deep tissue of patient's skin. Coplanar electrodes or electrodes tilted towards each other may be used with a low impedance material placed between the electrode/s and skin of patient. The low impedance material may be laid on patient's skin. Shallow layers of patient skin may overheat during treatment with large amount of energy because the electromagnetic field tends to travel through tissue with the lowest impedance. Supplemental low impedance material can improve the energy flow so that a relatively large amount of energy can be safely transmitted into the tissue. The material with low impedance may be a metal, alloys or other material with the same or lower impedance than epidermis and dermis.

Figure 11:
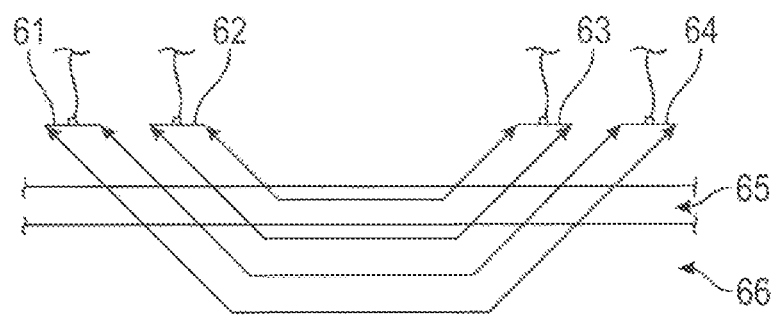
FIG. 11 is schematic diagram of induced currents inside tissue.

FIG. 11 shows an alternative design having phase controlled radiofrequency signals which may be used to improve targeting of induced electromagnetic energy into a predetermined depth of tissue. This system may include two or more pairs of electrodes, where the first pair of electrodes 62 and 63 is inside the second pair of electrodes 61 and 64. Electrode polarity between electrodes of the inner first pair fluctuates relative to the outer second pair with phase shift.

In the coplanar or tilted arrangement of electrodes, a shallow layer of the skin 65 such as epidermis and dermis is heated more when the electrodes are close together. A deep layer of the skin 66 such as hypodermis is heated more with increasing distance between the electrodes.

As the distances between electrodes of each pair are different, each pair induces an electromagnetic field at different depths of tissue. In a coplanar or tilted arrangement of electrodes, a greater distance between the electrodes induces greater energy in deep tissues of patient's skin. With the phase shift of these pairs it is possible to control the shape of induced electromagnetic energy and therefore heating of targeted tissue.

In FIG. 11, the induced electromagnetic field is represented by solid line arrows, with dashed line arrows representing induced movement of charged particles caused by phase shift of induced electromagnetic fields.

Phase shift can be used in array of electrodes, where each electrode is shifted in phase separately. With phase shift it is possible to decrease the difference of potentials of adjoining electrodes and therefore decrease the amount of induced electromagnetic field in shallow layers of skin. Even if the electrodes are close together phase shift may reduce unwanted heating or overheating in shallow layers of skin. Phase shifting may be used in a method for skin treatment by positioning first and second electrodes adjacent to the skin of the patient, with the electrodes not touching the skin, and providing airflow circulation between the electrodes and the skin. The electrodes transmit radio frequency waves into the skin, with the radio frequency waves heating the skin. The first electrode may transmit radio frequency waves having a phase different from the radio frequency waves transmitted by the second electrode.

Figure 12:
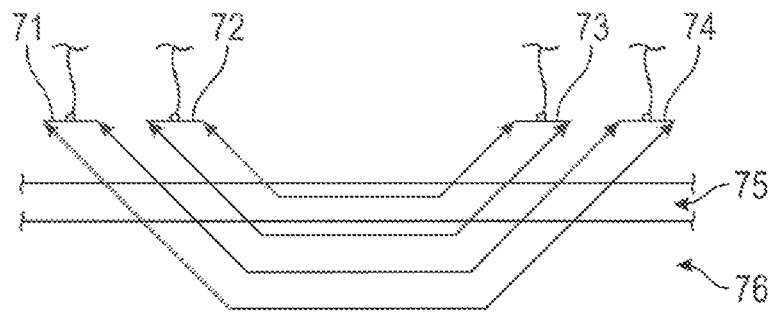
FIG. 12 is schematic diagram of induced currents inside tissue without use of an external magnetic field.
Figure 13:
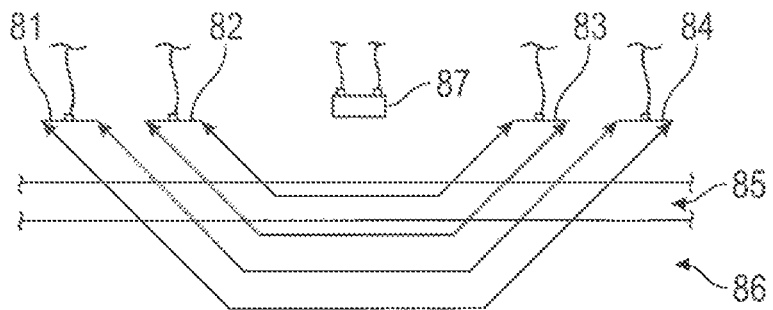
FIG. 13 is schematic diagram of induced currents inside tissue with use of external magnetic field.

Another system for providing targeted electromagnetic energy may use a supplemental magnetic field. FIG. 12 illustrates induced electromagnetic field inside the tissue without a supplemental magnetic field. The inner electrode pair of electrodes 72 and 73 induces an electromagnetic filed mainly inside a shallow layer of the skin 75. The outer electrode pair 71 and 74 induces an electromagnetic filed mainly in a deeper layer of the skin 76. FIG. 13 illustrates an induced electromagnetic field trajectory influenced by a permanent magnetic material or an inducing magnetic field from an electromagnet 87. The inner electrode pair of electrodes 82 and 83 induces an electromagnetic filed which is shifted from a shallow layer of the skin 85 more into a deeper layer of the skin 86. The outer electrode pair 81 and 84 induces an electromagnetic field mainly in the deeper layer of the skin 86.

An induced electromagnetic field can be deflected towards or away from the upper layers or lower layers of skin, depending on type of therapy. Based on the temperature of the skin, the microprocessor control unit can regulate the electromagnet to change the magnetic field and therefore influence the depth of the induced electromagnetic field in the skin of patient.

Figure 14:
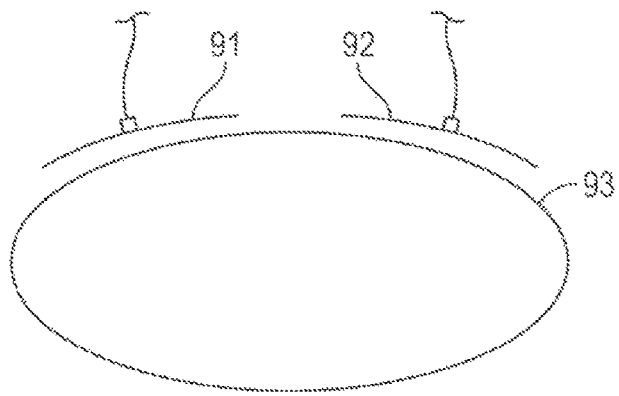
FIG. 14 is schematic diagram of a flexible electrode arrangement in transverse cross-section.

FIG. 14 illustrates a treatment system having malleable/flexible electrodes 91 and 92. In this design the applicator can be shaped according to the patient's shape to better match the individual. The distance between skin of the patient and applicator is therefore constant and heating of tissue is homogenous. This may help to eliminate possible temperature differences which might occur if there are any shape irregularities on human skin. Such a flexible applicator may be created from bipolar, monopolar or even unipolar system and one or more electrodes. The electrode(s) may be made of flexible material to insure that the electrode(s) are the same distance from the patient's skin and substantially parallel with skin of patient.

Systems and methods may provide improved skin surface treatment for large area sections and body parts with minimal need of personnel assistance during therapy. As shown in FIG. 12, a plurality of electrodes may be are arranged adjacent to each other. The electrodes may be interconnected and partially separated from each other by a carrier surface. If the electrodes are made of rigid material the distance between these individual carrier surfaces provide high flexibility of treatment area. Alternatively, the electrodes may be a flexible material. The electrodes may be selectively switched on and off during treatment, optionally with the electrodes switched so that adjoining electrodes will not be powered on at the same time.

Figure 15:
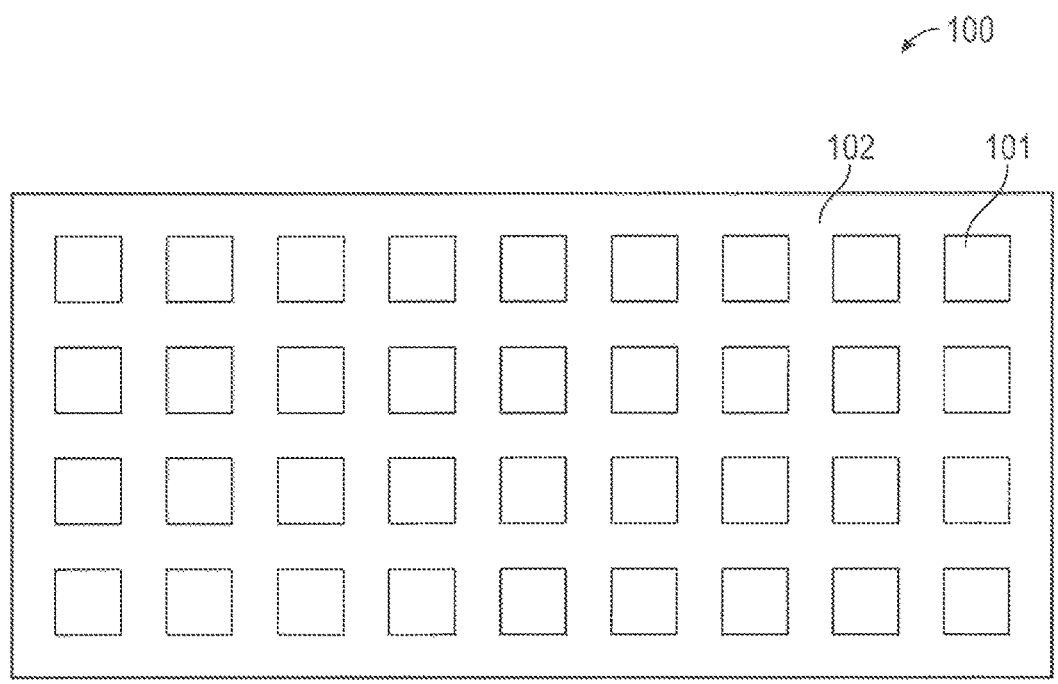
FIG. 15 is schematic diagram of arrangement of electrodes into a matrix.

As shown in FIG. 15, a system is provided for treating large areas or parts of the body 100 with minimal need of personnel assistance during therapy. Multiple electrodes 101 may be arranged adjacent to each other, with the electrode interconnected and partially separated from each other by carrier surface 102. If the electrodes are made of rigid material the spacing between the electrodes allows for flexible positioning of the electrodes on the body 100. However, preferably the electrodes are made from flexible material. The electrodes can be selectively switched on and off during treatment, optionally in a way so that adjoining electrodes are not powered on at the same time. This switching, if used, may be controlled by the microprocessor control unit and be set by the user in a user interface, or it may be set automatically based on treatment type.

Other forms of switching, such as random switching, or other algorithm switching of electrodes at specified electrode locations or distances, may also be use, to provide treatment to various depths.

The present system for skin treatment may be provided with an array of electrodes adjacent to the skin of the patient, with the electrodes not in contact with the skin of the patient. A microprocessor control unit is electrically connected, directly or indirectly, to the electrodes, with the electrodes transmitting radio frequency waves and the microprocessor selectively switching electrodes in the array on and off, optionally in a way so that adjoining electrodes are not powered on at the same time. A fixture may be used for holding the electrodes in a fixed position relative to the skin during at least part of the treatment process. The electrodes may be uniformly spaced apart into rows and columns, or aligned on concentric circles, or randomly arranged. The electrodes can be separated from the skin by an air gap or a spacer. The electrodes may be flexible, to conform to the skin or to a spacer, or to allow for greater versatility in positioning the electrodes. Temperature feedback control may be used to control skin temperature. Airflow may be provided between an electrode and the skin by positioning an air mover adjacent to the skin, for example using an air mover attached to the electrode or applicator, or an air tube connected to air source for moving air through the air tube to the patient's skin. The system may also be adapted to expose tissue to a supplemental magnetic field.

Figure 16:
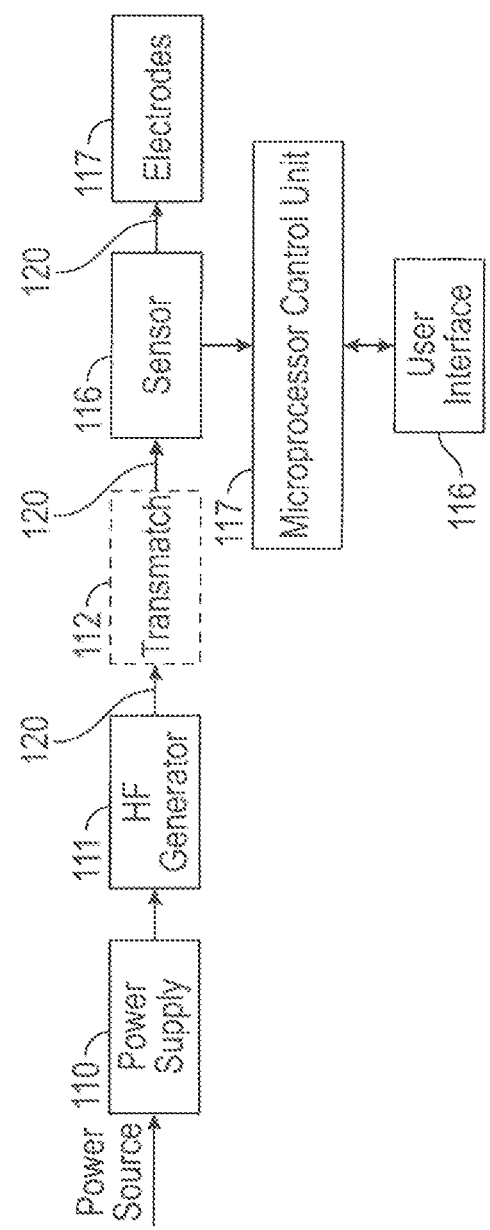
FIG. 16 is a block diagram of an apparatus for contactless skin and human tissue treatment with feedback control.

FIG. 16 depicts a block diagram of a device for contactless treatment of skin and subcutaneous tissue with feedback control of the input power. The device may include a power supply 110, an HF generator 111 and at least one electrode 117. The power supply 110 is connected to power source. The input power of the generated signal exceeds 40 W, and more preferably 80 W. The HF generator 111 may generate an electromagnetic field in the range of 1 MHz to 100 of GHz or optionally other frequencies as well. The 6.78, 13.56, 27.12 and 40.68 MHz; 2.45, 5.80 GHz and all other ISM bands avoid creating radio interference, as these frequencies are exclusively assigned as free or open frequencies.

The output signal from HF generator 111 is subsequently conducted to the electrodes 117, which may be positioned above the surface of the skin or applied on dielectric or insulating, non-conductive material which is in contact with the skin surface. The device for contactless skin treatment delivering RF energy into the patient is constructed as a symmetrical voltage power supply.

One or more sensors 116 are located between the HF generator 111 and at the least one electrode 117 to measure the values of at least one physical quantity, e.g. voltage, current or phase shift between physical quantities.

A transmatch 112 may optionally be connected by transmission cable 120 to the HF generator 111. The transmatch 112 adapts the signal from the RF generator 111 and based on reflection coefficient, measured for example by SWR meter, matches the impedance so as to optimize the power transfer and minimize the reflected signal load. Transmatch 112 is designed to withstand the high power load by using appropriate electromechanical components as is known in the art.

The output signal from transmatch 112 is provided to the electrodes 117 by transmission cables 120 where parasitic effects might occur. The undesirable parasitic effects are caused mainly by internal capacitance of the transmission cables. The parasitic capacitance is intensified by proximity of transmission cables, proximity with other conductors or high frequency signals. Parasitic effects cause reduction of the output power and distort the values measured by the sensor 116.

Significant reduction of parasitic capacitance can be achieved by its material composition and shading of the transmission cables 120. For example, the parasitic capacitance in the transmission cables is reduced or eliminated by using an electric cable with an outer cylindrical conductor and an internal conductor, where the space between them is filled with dielectric. Consequently, it is possible to measure values of at least one physical quantity inside the device more accurately, which allows the actual power delivered to the patient during therapy to be determined.

As shown in FIG. 16 the power supply 110, HF generator 111, transmatch 112 and sensor 116 can be communicatively coupled by microprocessor control unit 116. The microprocessor control unit 116 can provide communication with a user interface 118, which may be a touch screen on the device display.

The contactless device for treatment of the skin and human tissue by radio waves causes controlled heating of the designated areas on the patient. Based on the settings of a treatment device, for example as described in U.S. Patent Publication No. 2014/0249609, the radio waves cause selective heating of the dermis and/or the hypodermis. The controlled heating may lead to remodeling and/or downsizing of a volume of lipid-rich cells and/or remodeling of collagen tissue and/or remodeling of elastic fibers.

However the average impedance of the patient and treatment electrode changes during therapy due to reasons discussed below, which may cause inconsistency in the treatment. The impedance of the patient and treatment electrode can be compared to the impedance of a series circuit consisting of capacitor and resistor. Typical capacitance values ranges about 0.1-100 pF and resistance about 0.1-100 Ohms.

Since the patient is not in direct contact with the source of RF signal, the distance between patient and at least one electrode during the therapy permanently changes. The space between skin of the patient and at least one electrode is occupied by air gap or highly air permeable material. The distance between electrode and patient changes due to movements of the patient and either by biological rhythms such as breathing and heartbeat, which cause vibrations or movements of the treated tissue. Small movements and displacements during the therapy may cause impedance changes and the signal is not tuned for the whole time of the therapy. Therefore the output energy directed to the patient and absorbed by the patient may vary during the therapy.

The actual impedance depends besides the above mentioned factors and also on the shape and disposition of the patient and the amount of adipose tissue. In order to achieve optimal heating of treated skin or subcutaneous tissue in a patient with low resistance, it is necessary to increase the supplied power. The capacitance however causes formation of undesirable high voltage. The voltage can arise to about few kV in this area. Excessive voltages influence the quality of treatment process and may lead to inconsistency of treatment, with variable amounts of energy consumed in the epidermis layer. High voltage may also cause interference nearby electrical equipment.

To overcome these treatment irregularities, in one embodiment the sensor 4 measures the output values of at least one physical quantity (e.g. voltage, current) or phase shift between the physical quantity. In the case of using more than one electrode the sensor 4 may measure the values between different branches of the symmetrical signal cables leading to each electrode. The closer to the electrode the sensor is, the more precise the values can be measured.

However when the sensor 4 is placed near the electrode, the values can be out of scale of common measuring devices, since the output values can reach several kV. Therefore the sensor 4 may optionally be placed closely behind the transmatch 3. The values measured in this part are proportional to the values which are located close to the electrode of the device and are in the range from tens to several hundreds of Volts.

In another embodiment a look-up-table or a correction function can be used for determination of the output values of at least one physical quantity even if the values are measured in any part of the device. The look-up-table can be also used for determination of the output power delivered into the patient. In a similar way it is possible to determine the output power delivered into the patient by a correction function which corresponds to the transmission characteristics of the device e.g. $y=f(x)$, where input x represents the measured value of physical quantity inside the device. Thus by determination of the transmission characteristics it is possible to place the sensor 4 anywhere behind the transmatch so as to measure the output value and calculate the output power which is delivered into the patient.

The actual power delivered to the patient at a given time may be calculated according to the formula $P=U \cdot I \cdot \cos \varphi$. Where the U is voltage output value, I is current output value, $\cos \varphi$ is a phase shift between voltage and current. Summarization of such calculations may also provide the operator the true energy delivered into the patient during the therapy.

The measured values may be monitored and evaluated even by the sensor itself or by microprocessor control unit 6, which is electrically connected to the sensor 4. If the measured value exceeds a predetermined limit, a feedback signal is sent to the power supply 1 or HF generator 2 to adjust the input power. The signal may include information about exceeding a threshold both qualitative (e.g. yes/no) as well as the quantitative value (e.g. a real value). The signal from sensor 4 can be transmitted as optical information by e.g. optical fiber, so as to eliminate the effects of electromagnetic fields on the transmitted signal.

A method for contactless skin and human treatment starts by gradually increasing input power. The initial input power may be, for example 10 W, and consequently can be increased in predetermined intervals by an additional e.g. 10 W up to the maximum input power for a given therapy. Similarly, the input power can be added continuously. The size of the initial input power, the abrupt increase or rate of continuous increment can differ depending on the kind of therapy.

The input power is gradually increased until the sensor 4 measuring the output values measures an output value greater than the threshold. When the measured values exceed the threshold, the input power is reduced to either the last increment or by a value equal to the amount by which the last measured value exceeds the threshold. The threshold value of the output quantity can be adjusted based on type of therapy.

Since the impedance of the patient is dependent on any change in the distance between the electrode and patient's skin, the system is advantageously responsive to such change. Sampling frequency measurements of the output values of at least one physical quantity should be higher than 0.01 Hz.

The duration of therapy may be influenced by the calculated output power. As an example there may be a predetermined range of the output power for a specific kind of therapy. Time of therapy spent within the predetermined range will be counted into the real time of therapy. Therefore the therapies will be more precise, since the low/high powers will not be included into the treatment time.

According to the yet another embodiment the device for contactless skin and human tissue treatment is in communication with the sensor measuring the electric field intensity. Based on values measured by electric field intensity sensor the input power is adjusted. Communication links can be both wired and wireless. The sensor measuring the electric field intensity can be placed in close proximity to the skin of the patient or directly on the skin, or it can be built into the device or be an external device. If electric field intensity exceeds a predefined threshold, the input power is reduced to either by last increment or by a value equal to the amount by which the last measured value exceeds the threshold.

The skin temperature of the patient may optionally be measured, with input power adjusted based on a measured skin temperature. Optimal skin surface temperature during treatment is between 38° C.-48° C., preferably between 41°

C.-44° C. A sensor measuring the temperature of the skin of the patient can be placed in close proximity to the skin of the patient or directly on the skin. If the skin temperature exceeds a predefined threshold, the input power is reduced either by the last increment or by or by a value equal to the amount by which the last measured value exceeds the threshold. Similarly, it is possible to measure the temperature of the skin and/or human tissue by contactless methods as in e.g. WO2014114433, incorporated herein by reference. These may be contact or contactless or invasive method for obtaining detailed information about the temperature in the deep layers. A sensor measuring the temperature of the patient can be built-in or external device.

A distance sensor can measure the distance between the at least one electrode and patient. Based on the measured distance value, input power may be adjusted instantaneously. Optimal distance between electrode and patient varies depending on treatment frequency of radio wave, treated area, impedance, and time duration. The optimal distance may vary over a few tenths of a centimeter. If the distance exceeds a predefined threshold, the input power is reduced at either by last increment or by or by a value equal to the amount by which the last measured value exceeds the threshold. A sensor measuring the distance between the at least one electrode and patient can be built-in or an external device.

Alternatively a system may control the input power according to the received impedance values of the patient. A sensor measuring the impedance of the patient can be built-in or an external device.

Magnet treatment in combination with radiofrequency treatment may be represented by two independent treatment devices, e.g. one treating the target structure by radiofrequency waves and the second treating the target structure by magnetic field. Both devices may have a separate applicator for treating the target structure, or one applicator may be used by at least two devices, i.e. the applicator may be modular for a plurality of devices.

The aesthetic treatment device may include at least one HF frequency generator for providing energy for radiofrequency treatment and for providing energy for magnet treatment. In an alternative embodiment, the device may include at least one HF frequency generator for providing energy for radiofrequency treatment and at least one other independent frequency generator for providing energy for magnet treatment. The device may include plurality of applicators for providing separate radiofrequency or magnet treatments to the patient.

In alternative embodiment the applicator may provide a combination of radiofrequency and magnet treatment. In one embodiment, the applicator may include at least one radiofrequency electrode for providing radiofrequency treatment and at least one coil for providing magnet treatment. In another embodiment, the applicator may include at least one electrode for providing radiofrequency treatment and at least one coil providing magnet treatment, wherein the at least one RF source provides energy for both at least one electrode and at least one coil.

In still another embodiment the at least one RF source may provide the energy for the at least one coil providing magnet treatment wherein the at least one coil may be used as the at least one electrode. The essence is the far different stimulation frequencies which are used for RF treatment and magnet treatment. The coil in the high frequency field is similar to the electrode. This enables the coil to be the electrode for radiofrequency treatment. In the preferred embodiment a flat coil may be used as the electrode.

The frequencies for the radiofrequency treatment may be in the range of ones of MHz to hundreds of GHz, more preferably in the range of 13 MHz to 3 GHz, most preferably around 13.56 or 40.68 or 27.12 MHz or 2.45 GHz. The term "around" should be interpreted as in the range of 5% of the recited value. The impulse frequencies for the magnet treatment may be in the range of hundreds of Hz to hundreds of kHz, more preferably in the range of ones of kHz to tens of kHz, most preferably up to 10 kHz. However the repetition rate of the magnetic impulses may reach up to 700 Hz, more preferably up to 500 Hz, most preferably in the range of 1 to 300 Hz. The magnetic flux density of the magnet treatment is at least 0.1 T, more preferably at least 0.5 T, even more preferably at least 1 T, even more preferably at least 1.5 T, most preferably at least 2 T, or up to 7 Tesla on the coil surface.

The combination of the recited method may improve currently used applications in various aspects and the effect of the treatments may be significantly enhanced. The application of a radiofrequency electromagnetic field is combined with application of a magnetic field applied before, simultaneously or after the radiofrequency treatment. The magnetic field may be generated by a permanent magnet or electromagnet. The magnetic field may be constant in time or in the preferred application the magnetic field may be time-varying, more preferably a pulsed magnetic field may be used. The application of a magnetic field induces many benefits for radiofrequency treatment, such as applications inducing at least partial muscle contraction, myorelaxation effect or analgesic effect. The perfusion or metabolism may be improved as well.

The at least partial muscle contraction may induce enhanced effects on adipose tissue reduction by catabolism of the adipose tissue and burning energy from adipose tissue. The total adipose tissue reduction effect is enhanced by radiofrequency treatment.

Additionally, the at least partial muscle contraction may improve a blood flow and/or perfusion in the treated area. The improved blood flow may be caused by activation of muscle pump and/or by the muscle necessity of more oxygen due to the at least partial contraction. Due to increased blood flow and/or local perfusion, the risk of overheated muscle is limited or even eliminated. Further the homogeneity of the thermal field induced by thermal effect of radiofrequency treatment may be significantly enhanced and/or the temperatures may be well-balanced/compensated in the target treatment area. Still another benefit is prevention of creation any hot spot caused by steep thermal gradient.

Further the at least partial muscle contraction may improve the movement of lymphatic vessel and the lymph flow may be improved.

Due to improved blood flow, perfusion and/or lymph flow the metabolism may be improved. Additionally, the effect of radiofrequency treatment may be enhanced by improved metabolism, e.g. cellulite treatment, body shaping and/or contouring, skin tightening or skin rejuvenation. Further benefit may be reducing or eliminating the risk of panniculitis or local skin inflammation since any clustering of the treated adipocytes may be prevented by the improved metabolism. The improved blood and/or lymph flow may contribute the removing of the adipocytes. The removing of the adipocytes may be promoted by higher number of cells phagocytosing the adipocytes as well. Synergic effects of magnet and RF treatment significantly improves metabolism. Therefore the possibility of adverse event occurrence is limited and treatment results induced by the present invention are reached in shorter time period.

In the preferred application the RF and/or magnetic field may be modulated. In the most preferred application both stimulation signals are modulated. The magnetic stimulation may be modulated in the magnetic flux density domain, repetition rate domain, or impulse duration domain, to provide different treatment effects and to prevent adaptation of the target biological structure. The radiofrequency treatment may be modulated in the frequency domain, intensity domain and/or time domain to reach the most complexity and/or efficiency of the target treated biological structure. The modulation in the time domain may be changing the active and passive periods of stimulation, e.g. the radiofrequency treatment may include period with no stimulation, i.e. the radiofrequency treatment is not continual but the treatment is provided in pulses. The periods of no stimulation may vary and may be adjusted by the operator. Due to modulation during the treatment, different target biological structures may be treated in the different depth.

Using a pulse mode, the heat is local and typically limited to about 400 W. With the pulse mode, a high frequency field is applied in short intervals typically (50-2000 μs) and on various pulse frequencies (typically 50 to 1500 Hz). The maximum output with the continuous method is typically limited to 200 W.

The application may be contact or the preferred application of the invention the treatment may be applied contactless. Contactless application may avoid all biocompatibility factors which may occur during contact treatment. In the most preferred application the treatment may be provided by self-operated device. Hence the continual surveillance and/or control by the operator is not essential for correct and/or safe operation of the treatment device. Self-operated treatment may be provided by a hand-held applicator or the applicator may be fixed to stand-alone device. The self-operated treatment may be also enabled using various types of sensors in communication with the device for monitoring the treatment and/or the patient. The at least one sensor may be e.g. reactive sensor, electrochemical sensor, biosensor, biochemical sensor, temperature sensor, sorption sensor, pH sensor, voltage sensor, sensor for measuring distance of applicator from the patient surface and/or from the treated area, position sensor, motion detector, photo sensor, camera, sound detector, current sensor, sensor for measuring of specific human/animal tissue and/or any suitable sensors measuring biological parameters and/or combination thereof such as sensor for measuring dermal tensile forces, sensor for measuring the activity of the muscle, muscle contraction forces, tissue impedance or skin elasticity.

Further the homogeneity of the treatment may be improved by several approaches. A first approach may be represented by a moveable applicator providing the dynamic treatment to a larger target area. The dynamic treatment improves the homogeneity of applied treatment energy and additionally due to larger area the effect is uniform and/or well balanced. Static positioning of the applicator may be used as well. Another approach of improving homogeneity may be represented by using a bolus. The bolus may provide improved transmittance of the electromagnetic energy to the treated biological structures. Additionally, the bolus may prevent occurrence of hot spots within the treated area; the bolus may provide constant temperature to the target treated surface area; or the bolus may increase the homogeneity of the radiofrequency waves application by providing a homogenous medium for electromagnetic waves propagation not being influenced by the interface of the target treated area and an air. The bolus may profile the electromagnetic field to enhance the effect of the treatment. In still another approach an air gap may be between the applicator and the patient.

A current value of an operation parameter, e.g. voltage, electric current or magnetic flux density, may be determined by measuring via a suitable sensor or by deriving from a value of voltage source, e.g. an energy storage device or power source. The currently determined operation parameter is processed by a mathematic and/or signal processing method.

The treatment by magnetic and/or electromagnetic field may be in continuous or discrete modes. In one application the magnetic treatment may be applied in continual mode with no pauses and the electromagnetic treatment may be applied in pulsed mode to provide improved adipose tissue reduction caused by natural process and by the increased temperature. In another application the electromagnetic treatment may be applied continuously with no pauses and the magnetic treatment may be applied in pulsed mode to provide improved thermal reduction of adipose tissue and by improved metabolism due to improved blood flow. Both modes may be combined in various treatment sequences.

In the preferred application the treatment is started at the moment when the target biological structure reaches the predetermined temperature. The temperature in the target tissue may be up to 80° C., more preferably in the range of 37 to 60° C., even more preferably in the range of 40 to 45° C. The temperature may be adjusted based on the intended use, e.g. adipose tissue reduction, collagen production or muscle contraction. In an alternative application the intended use may be coagulation and/or ablation. The temperature in the target biological structure may be measured by invasive method, e.g. using an invasive probe; or by contact method, e.g. using thermocouple sensor; or by contactless method, e.g. using infrared sensor or camera. The temperature of the target biological structure may be determined by a mathematic method. The sensor for measuring the temperature in the target biological structure may be attached to the applicator.

A benefit of the application of magnet treatment and electromagnetic treatment may be causing an analgesic effect of the application and providing a possibility of treating a patient with higher sensitivity for thermal effects induced by electromagnetic treatment, i.e. patients with any predisposition inducing increased thermal sensitivity. The analgesic effect may be induced by magnet treatment by suitable repetition rates and it may be induced immediately during the magnet treatment. The analgesic effect may last up to several hours after magnet treatment. The magnetic flux density of the magnetic stimulation may preferably reach at least motor-threshold intensity inducing at least partial muscle contraction therefore the homogeneity of the thermal field is significantly enhanced.

Another benefit of application the magnet treatment may be causing a myorelaxation effect. The magnet treatment may be applied on spastic muscle structures to relieve the hypertonus of the muscle and improving the blood and/or lymph flow. Therefore relieving the hypertoned muscle may contribute to the analgesic effect and contribute to the acceptability of the treatment by the patient. The blood and/or lymph flow may be limited in the spastic muscles and the metabolism may be limited as well, meaning that the risk of clustering the treated target structures may be higher and possible adverse events may occur. The recited risks may be eliminated by the used of magnet treatment.

In one aspect of the invention, the treatment by magnetic field may be applied to the target structure before the radiofrequency treatment to prepare the target structure for following treatment by radiofrequency field. The effect of magnet treatment is to induce at least partial muscle contraction or to stimulate a muscle structure to increase a muscular tonus of the target structure. Both effects may provide a massage effect for the structure within the proximity of the target structure hence the blood and/or lymph circulation may be improved to promote local metabolism. The temperature may be locally increased by the improved blood flow and the target structure may accept the following radiofrequency treatment at significantly higher quality. Additionally, the collagen and/or elastin fibers may be remodeled or restored and/or its neogenesis may be improved to provide a younger, smoother and enhanced skin appearance.

Additionally, previous application may improve acceptability of the electromagnetic field by increasing the temperature of the skin and the transmittance of the electromagnetic field may be improved due to less value of skin impedance. Further the radiofrequency may penetrate deeper target structures relative to treatment without a preceding magnet treatment of the target structure and/or area.

Another benefit may be releasing the adipose tissue in the muscle by muscle contraction and/or by temperature increase causing better liquidity of adipose tissue. Still another benefit of the at least partial muscle contraction may be mechanical breaking large adipose tissue bulks into smaller bulks which may be easier metabolism of the adipose tissue and/or the smaller adipose tissue bulks may be removed faster by the lymphatic and/or blood flow. Due to improved metabolism and/or circulation the cellulite may be treated in a short time and the visual effect on skin appearance may be significantly enhanced.

In another aspect of the invention, the treatment by magnetic field may be applied to the target structure simultaneously with the radiofrequency treatment to improve effects of the electromagnetic treatment inducing heat in the target structure.

The simultaneous application of magnet treatment and radiofrequency treatment may be in two modes: a first mode may generate the magnet impulses while radiofrequency treatment is active or another mode may generate radiofrequency treatment while the magnet treatment is not in an active stimulation period, i.e. the period of magnet treatment and radiofrequency treatment alternates. Both modes amplify the resulting effect of the treatment. Therefore the results are achieved in significantly shorter time than the same results achieved by separate applications of the radio frequency and magnet treatments.

The simultaneous method of magnet treatment and radiofrequency treatment of the target tissue may increase the peak magnetic component of the entire treatment resulting in improved heating of the target structure including containing higher water volume, e.g. skin. Due to increased temperature of skin, the production and/or remodeling of collagen and/or elastin fibers may be improved and the skin may be provided with a younger, smoother and enhanced appearance. The effect of overheating the muscle is reduced by the improved blood flow.

In still another aspect of the invention, the treatment by magnetic field may be applied to the target structure after the treatment by electromagnetic field to enhance and/or contribute to the effects of radiofrequency treatment by influencing the target structure by magnetic field.

The magnetic field may treat the target structure to cause at least partial muscle contraction proximate to the target structure to improve blood flow and provide homogenous temperature distribution at high quality after creating a temperature distribution at lower quality by radiofrequency treatment.

All of the methods may be provided by the above recited technical solutions. The above mentioned methods may be used separately or in any combination.

Novel systems and methods have been described. The invention should be interpreted in the broadest sense, hence various changes and substitutions may be made of course without departing from the spirit and scope of the invention. The invention, therefore, should not be limited, except by the following claims and their equivalents.

The invention claimed is:

1. A method of treatment of a target biological structure of a patient using a treatment device which includes a connection to an energy source, a high-frequency generator, a radiofrequency electrode, an energy storage device electrically connected to a switching device and a magnetic field generating device, comprising:
   a. charging the energy storage device from the energy source;
   b. providing energy from the energy storage device to the magnetic field generating device to generate a time-varying magnetic field;
   c. applying the time-varying magnetic field to the patient;
   d. providing energy from the energy source to the high-frequency generator in order to provide the energy to the radiofrequency electrode;
   e. generating radiofrequency waves with a frequency of at least 1 MHz by the radiofrequency electrode;
   f. applying the radiofrequency waves to the patient; and
   g. heating the target biological structure by the radiofrequency waves;
   h. wherein the magnetic field has a repetition rate in a range of 1 to 100 Hz;
   i. wherein a voltage drop between successive peak amplitudes in the energy storage device is up to 21%.

2. A method for treating a biological structure of a patient by a time-varying magnetic field and radiofrequency waves, comprising:
   a. providing energy from an energy source to an energy storage device and/or to a high-frequency generator;
   b. providing energy from the energy storage device to a magnetic field generating device in order to generate the time-varying magnetic field with a magnetic flux density in a range of 0.1 to 7 T, a repetition rate in a range of 1 to 700 Hz and with an impulse duration in a range of 10 to 900 μs;
   wherein the magnetic field generating device includes a conductor diameter less than 3 mm;
   c. providing energy from the high-frequency generator to a balun transformer in order to convert an unbalanced radiofrequency signal to a balanced radiofrequency signal and providing the balanced radiofrequency signal to a transmatch in order to adjust an impedance of at least one radiofrequency electrode to correspond with an impedance of the biological structure of the patient; and
   d. generating radiofrequency waves with a frequency in a range of 1 MHz to 900 GHz and with energy up to 400 W by the at least one radiofrequency electrode;
   e. applying the radiofrequency waves simultaneously with the time-varying magnetic field to the patient; and f. remodeling a target biological structure by simultaneous heating the biological structure and contracting a muscle of a target body area.

3. The method of claim 2 wherein the magnetic field generating device includes a litz-wire.

4. The method of claim 2 wherein a voltage drop between two successive peak amplitudes output from the energy storage device is not higher than 21%.

5. The method of claim 2 wherein the energy storage device is in a serial connection with the magnetic field generating device.

6. The method of claim 2 further comprising directing a cooling media in a direction parallel to the magnetic field generating device.

7. The method of claim 2 further comprising directing a cooling media over at least upper and lower sides of the magnetic field generating device.

8. The method of claim 2 with the magnetic field generating device including a blower for directing a cooling media and wherein the blower is on a circumference of the magnetic field generating device.

9. The method of claim 2 further comprising operating the device including the magnetic field generating device in order to maintain a temperature of a casing of the magnetic field generating device up to 43° C.

10. A method for treatment of a biological structure of a patient by a time-varying magnetic field and radiofrequency waves, comprising:
a. providing energy from an energy source to an energy storage device and/or to a high-frequency generator;
b. providing energy from the energy storage device to a magnetic field generating device in order to generate the time-varying magnetic field;
c. applying the time-varying magnetic field to the patient;
d. providing energy from the high-frequency generator to a transmatch in order to adjust an impedance of a radiofrequency electrode to correspond with an impedance of a biological structure of the patient;
e. generating the radiofrequency waves by the radiofrequency electrode with a frequency of at least 1 MHz;
e. applying the radiofrequency waves to the patient; and
f. heating the biological structure by the radiofrequency waves.

11. The method of claim 10 wherein the magnetic field generating device includes a litz-wire having a conductor diameter less than 3 mm.

12. The method of claim 10 wherein a voltage drop between two successive peak amplitudes output from the energy storage device is not higher than 21%.

13. The method of claim 10 wherein the energy storage device is in a serial connection with the magnetic field generating device.

14. The method of claim 10 wherein the magnetic field generating device includes a litz-wire, further comprising providing energy from the high-frequency generator to a balun transformer in order to convert an unbalanced radiofrequency signal to a balanced radiofrequency signal.

15. The method of claim 10 further comprising directing a cooling media in a direction parallel to the magnetic field generating device.

16. The method of claim 10 further comprising directing a cooling media over at least upper and lower sides of the magnetic field generating device.

17. The method of claim 10 further comprising directing a cooling media on a circumference of the magnetic field generating device.

18. The method of claim 10 further comprising operating a treatment device including the magnetic field generating device in order to maintain a temperature of a casing of the magnetic field generating device up to 43° C.

19. A method for treating a biological structure of a patient by a time-varying magnetic field and radiofrequency waves comprising:
a. providing energy from an energy source to an energy storage device and/or to a high-frequency generator;
b. providing energy from the energy storage device to a magnetic field generating device in order to generate the time-varying magnetic field with a magnetic flux density in a range of 0.15 to 7 T, a repetition rate in a range of 1 to 700 Hz, and with an impulse duration in a range of 10 to 900 µs;
c. providing energy from the high-frequency generator to a radiofrequency electrode in order to generate the radiofrequency waves with a frequency in a range of 1 MHz to 900 GHz;
d. applying the time-varying magnetic field to at least one body region including thighs, buttocks, abdomen, hips or arms of the patient in order to cause a muscle contraction and the radiofrequency waves heating the at least one body region of the patient; and
e. using a signal from a sensor measuring a physical quantity including one or more of voltage, current, a phase shift, a magnetic flux density, a temperature, an electric field intensity, a distance or an impedance in order to adjust an output power applied to the patient.

20. The method of claim 19 wherein the magnetic field generating device includes a conductor diameter less than 3 mm.

21. The method of claim 19 wherein the magnetic field generating device includes a litz-wire.

22. The method of claim 19 wherein a voltage drop between two successive peak amplitudes output from the energy storage device is not higher than 21%.

23. The method of claim 19 wherein the energy storage device is in a serial connection with the magnetic field generating device.

24. The method of claim 19 further comprising directing a cooling media in a direction parallel to the magnetic field generating device.

25. The method of claim 19 further comprising directing a cooling media by a blower on a circumference of the magnetic field generating device.

26. The method of claim 19 further comprising operating a treatment device including the magnetic field generating device to maintain a temperature of a casing of the magnetic field generating device up to 43° C.

27. The method of claim 19 wherein the sensor is in a treatment device including the magnetic field generating device and/or the radiofrequency electrode.

28. The method of claim 19 further comprising causing a repeated muscle contraction.

29. The method of claim 19 further comprising applying the radiofrequency waves with energy up to 400 W.

30. The method of claim 19 further comprising providing energy from the high-frequency generator to a balun transformer in order to convert an unbalanced radiofrequency signal to a balanced radiofrequency signal and providing the balanced radiofrequency signal to a transmatch in order to adjust an impedance of a radiofrequency electrode to correspond with an impedance of the biological structure of the patient.

* * * * *

UNITED STATES PATENT AND TRADEMARK OFFICE
CERTIFICATE OF CORRECTION

PATENT NO. : 10,124,187 B2  
APPLICATION NO. : 15/151012  
DATED : November 13, 2018  
INVENTOR(S) : Tomáš Schwarz and Ondra Prouza Page 1 of 1

It is certified that error appears in the above-identified patent and that said Letters Patent is hereby corrected as shown below:

On the Title Page

At item (63) Related U.S. Application Data, delete the text beginning with "Continuation-in-part of application No. 15/073,318" to and ending "which is a continuation-in-part of application No. 14/700,349, filed on Apr. 30, 2015, now Pat. No. 9,446,258." and insert --Continuation-in-part of application No. 15/073,318 filed on Mar. 17, 2016, now Pat. No. 9,919,161, and a continuation-in-part of application No. 14/951,093 filed on Nov. 24, 2015, now abandoned, and a continuation-in-part of application No. 14/926,365, filed on Oct. 29, 2015, now abandoned, and a continuation-in-part of application No. 14/789,658, filed on Jul. 1, 2015, now Pat. No. 9,636,519. Application No. 15/151,012 is also a continuation-in-part of application No. 14/873,110, filed on Oct. 1, 2015, now Pat. No. 9,586,057, which is a continuation of application No. 14/789,156, filed on Jul. 1, 2015, now abandoned. Application No. 15/151,012 is also a continuation-in-part of application No. 15/099,274, filed on Apr. 14, 2016, now abandoned, and a continuation-in-part of application No. 14/697,934, filed on Apr. 28, 2015, now Pat. No. 9,468,774, and a continuation-in-part of application No. 14/700,349, filed on Apr. 30, 2015, now Pat. No. 9,446,258.-- therefor.

Signed and Sealed this  
Seventh Day of May, 2019

Andrei Iancu  
*Director of the United States Patent and Trademark Office*